US005762928A

United States Patent [19]
Bolkan et al.

[11] Patent Number: 5,762,928
[45] Date of Patent: Jun. 9, 1998

[54] BIOCONTROL AGENT FOR GREEN MOLD DISEASE OF MUSHROOMS

[75] Inventors: Hasan Bolkan; Dennis J. Larsen, both of Davis, Calif.

[73] Assignee: Campbell Soup Company, Camden, N.J.

[21] Appl. No.: 869,998

[22] Filed: Jun. 5, 1997

[51] Int. Cl.$^6$ .................................................. C12N 1/20
[52] U.S. Cl. ........................... 424/93.47; 435/253.3
[58] Field of Search ...................... 424/93.47; 435/253.3

[56] References Cited

U.S. PATENT DOCUMENTS

| | | | |
|---|---|---|---|
| 3,819,829 | 6/1974 | Mann | 424/93.46 |
| 4,345,403 | 8/1982 | Giovannetti | 47/1.1 |
| 4,663,162 | 5/1987 | Kado et al. | 424/93.46 |
| 5,049,379 | 9/1991 | Handelsman et al. | 424/115 |
| 5,061,490 | 10/1991 | Paau et al. | 424/93.47 |
| 5,283,060 | 2/1994 | Shieh | 424/418 |
| 5,503,647 | 4/1996 | Dahlberg et al. | 47/1.1 |

OTHER PUBLICATIONS

Frändberg et al., "Chitinolytic Properties of *Bacillus pabuli* K1," *J. of Applied Bacteriology*, vol. 94, pp. 361–367, 1994.

*Primary Examiner*—Jean C. Witz
*Attorney, Agent, or Firm*—Banner & Witcoff

[57] ABSTRACT

A biological control agent for controlling green mold disease caused by the fungus *Trichoderma harzianum*. An effective amount of a composition comprising *Pseudomonas aeruginosa* and mutants thereof which retain the characteristic of preventing green mold growth is applied to compost, spawn, or supplement, to prevent or inhibit the growth of green mold.

6 Claims, No Drawings

BIOCONTROL AGENT FOR GREEN MOLD DISEASE OF MUSHROOMS

FIELD OF THE INVENTION

The invention is directed to a biological control agent for controlling green mold diseases caused by the fungus *Trichoderma harzianum*.

BACKGROUND OF THE INVENTION

There are at least 32 species within the genus Trichoderma. Trichoderma fungi are found everywhere including forest and agricultural soils, paper, wood, sawdust, and organic debris. *Trichoderma harzianum* is the species that causes green mold disease in mushroom production.

Green mold disease is a common disease of edible Agaricus mushrooms. Losses caused by green mold disease are usually the result of the *T. harzianum* taking over the mushroom bed and out-competing the Agaricus for available nutrients and space. Green mold infection typically results in an area of the bed containing a patch of green mold without any mushrooms to harvest. Thus, the higher the degree of bed infestation, the lower the mushroom production. *T. harzianum* can but usually will not infect mushrooms. Mushrooms infected with green mold disease are not marketable.

Green mold disease can significantly reduce or eliminate production as well as negatively impact mushroom quality. Losses on an individual mushroom house can range from 1 to 100% and are directly proportional to the degree the bed is infected by the green mold disease. Low losses occur when the green mold infection is present in only small areas of the bed. Total losses occur when all the beds in a mushroom house are "cooked off" or steam sterilized to kill the green mold infection before any mushrooms can be harvested. Total losses are rare but do occur.

Current control techniques involve mushroom house sanitation and the application of salt or chlorine to green mold disease spots as they appear on the beds. The synthetic fungicide BENLATE is often used. However, obtaining good bed coverage and consistent efficacy results is difficult with BENLATE; thus, BENLATE does not provide satisfactory fungal control. In addition, there are labor safety concerns with using chemicals such as BENLATE, and the cost of such chemicals can be high. Further, chemical treatments still result in a loss of mushroom growth in the areas affected by the green mold disease and treated with the chemicals.

The disease is currently epidemic in North America and European mushroom production areas. In Europe, the reported strains are Th1, Th2 and Th3, with the most virulent being 112. In the United States, the reported strains are Th11, Th3 and Th4, with the most virulent being Th4. See Romaine, P. C. et al. "Mushroom Green Mold: Cause Edaphic Factors & Control," *Mushroom News*, pp 20–23, November 1996, and Morris, E. and O. Doyal "A Profile of Trichoderma Species II-Mushroom Growing Units," *Science and Cultivation of Edible Fungi*, Ed. Elliott, pp. 619–625 (1995).

SUMMARY OF THE INVENTION

The present invention is directed to a method for inhibiting green mold disease comprising applying to mushroom compost, supplement, and/or spawn an effective amount of a composition comprising *Pseudomonas aeruginosa* and mutants thereof which retain the characteristic of preventing green mold growth.

The present invention is further directed to a biological inoculant for the prevention of green mold growth comprising *Pseudomonas aeruginosa* and mutants thereof which retain the characteristic of preventing green mold growth and a suitable carrier.

DETAILED DESCRIPTION OF THE PREFERRED EMBODIMENTS

Applicants discovered that bacteria isolated from brown mushroom compost are antagonistic to the growth of *Trichoderma harzianum* or green mold disease. This discovery was made, in part, by the observation that green mold disease rarely was a problem on brown mushroom compost. Numerous bacteria (79) were isolated and challenged against *Trichoderma harzianum* in vitro. Through testing and elimination it was discovered that the bacteria, *Pseudomonas aeruginosa*, were found to inhibit the growth of the green mold disease when both the bacteria and green mold fungus were grown simultaneously on agar plates. When these bacteria were added to mushroom compost in concentrations of $1 \times 10^6$ CFU (colony forming units) per pound of compost, they suppressed the growth of the green mold resulting in 100% disease control and good yields of mushrooms.

The present invention utilizes a composition containing an effective amount of *Pseudomonas aeruginosa* or mutants thereof which retain the characteristic of preventing green mold growth. A suitable carrier is also present in the composition. The composition is used to inoculate mushroom compost, supplement, and/or spawn in order to inhibit or prevent growth of green mold disease.

There are many advantages to using a composition containing the bacteria or mutants thereof. By inoculating the composition into mushroom compost, the bacteria will reduce or eliminate the need for chemical treatment to control green mold disease. The use of the composition will also generate cost savings or cost avoidance by reducing mushroom production costs and by reducing or eliminating yield losses due to the disease. In addition, the bacteria is not toxic to the mushrooms.

To enable others to obtain a culture of the *Pseudomonas aeruginosa*, samples were deposited at the American Type Culture Collection Patent Collection, Rockville, Md. on Apr. 16, 1997, and granted accession number 55953. The strain was isolated from brown mushroom compost.

The bacteria are isolated from any suitable source in any suitable manner. *P. aeruginosa* is typically isolated from brown mushroom compost. For example the bacteria may be isolated by blending brown mushroom compost with sterile water, straining the slurry through a sterile cheese cloth, diluting the strained liquid, plating the dilution(s) on BSM (Bacillus semi-selective media) and ASM (Actinomycete semi-selective media); and recovering the isolate. The bacteria grows on either media.

After the bacteria are isolated, they are combined with a suitable (agronomically-acceptable) carrier such as vermiculite, perlite, charcoal, or water. The bacteria may also be encapsulated or freeze dried and used as powders, particles, granules, suspensions, slurries or concentrates. Methods of encapsulation and freeze drying are known in the art and any suitable method is contemplated. In addition to the carrier, effective amounts of nutrients, preservatives, and vitamins may be included as desired.

The bacteria and suitable carrier may be incorporated directly into the compost, supplement, spawn, or combinations thereof, by any suitable technique. For instance, the composition may be applied as a spray, dust, granule, or the like. Typically, in mushroom houses, the composition is applied as a spray.

Preferably the bacteria is incorporated directly into mushroom compost, usually during spawning or casing, as an aqueous spore suspension. The process of inoculating compost with particulate matter colonized with mushroom mycelia (spawn) through it, whereby the compost is then colonized by the mycelium, is known as spawning. Mushroom spawn is generally made from sterilized grain that is inoculated with pure cultures of the desired mushroom strain. Mixing the colonized compost with, or covering by a layer of, nutrient poor material is known as casing. The mycelium proceeds to colonize the casing layer, and once the casing layer is colonized, the mycelium in this nutrient poor environment produces fruiting bodies.

Instead of incorporating the bacteria into the compost, the bacteria may be incorporated into mushroom supplements or into the spawn. The supplements or spawn may then be cultivated or sold to others for cultivation.

The compost, supplements or spawn is inoculated with an effective amount of the bacteria to inhibit the growth of green mold disease. Although not intended to be limiting, at least 100,000 and usually at least 1 million colonies forming units per pound of compost are used. Aqueous formulations include liquids having from about $10^5$ to $10^9$ colonies/ml which is applied to the compost in amounts of 1.5 to 5 gallons of spore suspension per 6800–7500 pounds of compost.

EXAMPLES

The invention will be further described by reference to the following examples. These examples should not be construed in any way as limiting the invention to anything less than that which is disclosed or which could have been obvious to anyone skilled in the art.

Example 1

*Pseudomonas aeruginosa* were isolated by blending 100 g brown mushroom compost with 100 m sterile water. The resulting slurry was strained through sterile cheese cloth. The stained liquid was diluted with sterile water to 1:10, 1:100, and 1:1000 dilutions. 0.1 ml of the dilutions were plated on BSM (Bacillus semi-selective media) and ASM (Actinomycete semi-selective media). The isolate B8-96CSC was recovered from a 1:1000 dilution on BSM media. This isolate was designated ATCC accession number 55953.

Example 2

The bacteria were applied to 5 of 14 mushroom beds in each of five houses. The untreated beds were used as controls. The beds were 688 square feet (4 feet wide, 122 feet in length and 8 inches high.) The beds contained approximately 6840 pounds of compost at 68% moisture. 10 liters of water containing 14 plates of bacteria (Example 1) were added to each mushroom bed. The quantity of bacteria was approximately $1 \times 10^6$ colonies per ml. The following results were noted:

There was no reduction in yield mushrooms as measured by pounds/$ft^2$ compared to untreated houses.

The number of *T. harzianum* strikes was reduced by 77%.

number of treated beds=25, number of green mold strikes=30 number of control beds=45, number of green mold strikes=129

The average size of the individual *T. harzianum* strikes was reduced by 19%.

average size of treated strikes=352 $in^2$ (data from 3 houses)

average size of control strikes=435 $in^2$ (data from 3 houses)

The bacteria delayed the first appearance of green mold disease on the beds by 1 day.

It will be apparent to those skilled in the art that various modifications and variations can be made in the compositions and methods of the present invention without departing from the spirit or scope of the invention. Thus, it is intended that the present invention cover the modifications and variations of this invention provided they come within the scope of the appended claims and their equivalents.

We claim:

1. A method for inhibiting green mold disease caused by *Trichoderma harzianum* in mushrooms comprising administering to said mushrooms an effective amount of a composition comprising a strain of *Pseudomonas aeruginosa* having all the identifying characteristics of *Pseudomonas aeruginosa* ATCC 55953.

2. The method of claim 1 wherein the composition is an aqueous solution.

3. The method of claim 1 wherein the composition is incorporated into mushroom supplement.

4. The method of claim 1 wherein the composition is incorporated into mushroom spawn.

5. A composition for inhibiting green mold disease caused by *Trichoderma harzianum* in mushrooms comprising an effective amount of a strain of *Pseudomonas aeruginosa* having all the identifying characteristics of *Pseudomonas aeruginosa* ATCC 55953 and an agriculturally acceptable carrier.

6. The method of claim 1 wherein the composition is incorporated into mushroom compost.

* * * * *

UNITED STATES PATENT AND TRADEMARK OFFICE
CERTIFICATE OF CORRECTION

PATENT NO. : 5,762,928
DATED : June 9, 1998
INVENTOR(S) : Bolkan, et al

It is certified that error appears in the above-identified patent and that said Letters Patent is hereby corrected as shown below:

At Column 1, line 53, please change "112" to --Th2--.

Signed and Sealed this

Eighth Day of September, 1998

Attest:

BRUCE LEHMAN

*Attesting Officer*     *Commissioner of Patents and Trademarks*